United States Patent
Slate et al.

(10) Patent No.: US 8,177,749 B2
(45) Date of Patent: May 15, 2012

(54) CASSETTE FOR A HIDDEN INJECTION NEEDLE

(75) Inventors: John B. Slate, San Diego, CA (US);
Michael W. Burk, San Marcos, CA (US); Richard J. Koerner, San Diego, CA (US); Corey M. Magers, Encinitas, CA (US); Andrew C. Barnes, San Diego, CA (US)

(73) Assignee: Avant Medical Corp., Thousand Oaks, CA (US)

( * ) Notice: Subject to any disclaimer, the term of this patent is extended or adjusted under 35 U.S.C. 154(b) by 56 days.

(21) Appl. No.: 12/123,888

(22) Filed: May 20, 2008

(65) Prior Publication Data

US 2009/0292246 A1 Nov. 26, 2009

(51) Int. Cl.
*A61M 37/00* (2006.01)

(52) U.S. Cl. ........................................ 604/131

(58) Field of Classification Search ............ 604/131, 604/187, 167, 95.01, 195, 197, 198, 110, 604/192; 606/167; 128/DIG. 1
See application file for complete search history.

(56) References Cited

U.S. PATENT DOCUMENTS

| | | |
|---|---|---|
| 3,720,211 A | 3/1973 | Kyrias |
| 3,964,481 A | 6/1976 | Gourlandt et al. |
| 4,108,177 A | 8/1978 | Pistor |
| 4,421,107 A | 12/1983 | Estes et al. |
| 4,613,328 A | 9/1986 | Boyd |
| 4,617,016 A | 10/1986 | Blomberg |
| 4,636,201 A | 1/1987 | Ambrose et al. |
| 4,986,818 A | 1/1991 | Imbert et al. |
| 5,013,299 A | 5/1991 | Clark |
| 5,024,616 A * | 6/1991 | Ogle, II ..................... 604/192 |
| 5,085,641 A | 2/1992 | Sarnoff et al. |
| 5,092,843 A | 3/1992 | Monroe et al. |
| 5,098,400 A | 3/1992 | Crouse et al. |
| 5,114,404 A | 5/1992 | Paxton et al. |

(Continued)

FOREIGN PATENT DOCUMENTS

WO 8606967 A1 12/1986

(Continued)

OTHER PUBLICATIONS

U.S. Appl. No. 12/178,447, filed Jul. 23, 2008, entitled, "System and Method for an Injection Using a Syringe Needle", Slate, et al.

(Continued)

*Primary Examiner* — Nicholas Lucchesi
*Assistant Examiner* — Brooke Matney
(74) *Attorney, Agent, or Firm* — SorinRoyerCooper LLC

(57) ABSTRACT

A system for injecting a fluid medicament into a patient includes a drive mechanism, and a cassette loaded with a pre-filled hypodermic syringe. When the cassette is loaded, the syringe is held firmly inside and the cassette can be selectively engaged with the drive mechanism. The drive mechanism has two motors. A first motor initially moves the hypodermic syringe from a position inside the cassette where its needle is concealed, to a position where the needle extends from the cassette for insertion into a patient for an injection. With the needle inserted, a second motor pushes the syringe stopper to expel a fluid medicament from the syringe. After an injection, the first motor withdraws the syringe back into concealment inside the cassette, to again firmly hold the syringe on the cassette. The cassette and syringe, in combination, can then be removed from the drive mechanism and discarded.

6 Claims, 2 Drawing Sheets

U.S. PATENT DOCUMENTS

| | | |
|---|---|---|
| 5,176,643 A | 1/1993 | Kramer et al. |
| 5,221,268 A | 6/1993 | Barton et al. |
| 5,300,029 A | 4/1994 | Denance |
| 5,318,522 A | 6/1994 | D'Antonio |
| 5,352,196 A | 10/1994 | Haber et al. |
| 5,354,286 A | 10/1994 | Mesa et al. |
| 5,425,715 A | 6/1995 | Dalling et al. |
| 5,456,670 A | 10/1995 | Neer et al. |
| 5,478,316 A | 12/1995 | Bitdinger et al. |
| 5,540,664 A | 7/1996 | Wyrick |
| 5,569,190 A | 10/1996 | D'Antonio |
| 5,578,014 A | 11/1996 | Erez et al. |
| 5,584,815 A | 12/1996 | Pawelka et al. |
| 5,593,390 A | 1/1997 | Castellano et al. |
| 5,599,302 A | 2/1997 | Lilley et al. |
| 5,681,291 A | 10/1997 | Galli |
| 5,690,618 A | 11/1997 | Smith et al. |
| 5,695,472 A | 12/1997 | Wyrick |
| 5,709,662 A | 1/1998 | Olive et al. |
| 5,720,729 A | 2/1998 | Kriesel |
| 5,728,074 A | 3/1998 | Castellano et al. |
| 5,746,714 A | 5/1998 | Salo et al. |
| 5,807,346 A | 9/1998 | Frezza |
| 5,843,036 A | 12/1998 | Olive et al. |
| 5,868,711 A | 2/1999 | Kramer et al. |
| 5,911,703 A | 6/1999 | Slate et al. |
| 5,919,159 A | 7/1999 | Lilley et al. |
| 5,921,963 A | 7/1999 | Erez et al. |
| 5,957,897 A | 9/1999 | Jeffrey |
| 6,019,745 A | 2/2000 | Gray |
| 6,019,747 A | 2/2000 | McPhee |
| 6,099,503 A | 8/2000 | Stradella |
| 6,149,626 A | 11/2000 | Bachynsky et al. |
| 6,159,184 A | 12/2000 | Perez et al. |
| 6,171,276 B1 | 1/2001 | Lippe et al. |
| 6,171,283 B1 | 1/2001 | Perez et al. |
| 6,183,442 B1 | 2/2001 | Athanasiou et al. |
| 6,203,530 B1 | 3/2001 | Stewart, Sr. |
| 6,210,369 B1 | 4/2001 | Wilmot et al. |
| 6,241,709 B1 | 6/2001 | Bechtold et al. |
| 6,270,479 B1 | 8/2001 | Bergens et al. |
| 6,280,421 B1 | 8/2001 | Kirchhofer et al. |
| 6,290,683 B1 * | 9/2001 | Erez et al. .................... 604/273 |
| 6,344,030 B1 | 2/2002 | Duchon et al. |
| 6,344,032 B1 | 2/2002 | Perez et al. |
| 6,371,939 B2 | 4/2002 | Bergens et al. |
| 6,406,456 B1 | 6/2002 | Slate et al. |
| 6,447,482 B1 | 9/2002 | Rønborg et al. |
| 6,454,743 B1 | 9/2002 | Weber |
| 6,520,928 B1 | 2/2003 | Junior |
| 6,544,234 B1 | 4/2003 | Gabriel |
| 6,547,755 B1 | 4/2003 | Lippe et al. |
| 6,599,272 B1 | 7/2003 | Hjertman et al. |
| 6,641,561 B1 | 11/2003 | Hill et al. |
| 6,645,169 B1 | 11/2003 | Slate et al. |
| 6,645,177 B1 | 11/2003 | Shearn |
| 6,648,858 B2 | 11/2003 | Asbaghi |
| 6,652,483 B2 | 11/2003 | Burk et al. |
| 6,656,163 B1 | 12/2003 | Marshall et al. |
| 6,656,164 B1 | 12/2003 | Smith |
| 6,669,664 B2 | 12/2003 | Slate et al. |
| 6,692,469 B1 | 2/2004 | Weekes et al. |
| 6,746,427 B2 | 6/2004 | Duchon et al. |
| 6,752,787 B1 | 6/2004 | Causey, III et al. |
| 6,767,336 B1 | 7/2004 | Kaplan |
| 6,770,052 B2 | 8/2004 | Hill et al. |
| 6,796,957 B2 | 9/2004 | Carpenter et al. |
| 6,805,686 B1 | 10/2004 | Fathallah et al. |
| 6,808,507 B2 | 10/2004 | Roser |
| 6,835,193 B2 | 12/2004 | Epstein et al. |
| 6,890,319 B1 | 5/2005 | Crocker |
| 6,979,316 B1 | 12/2005 | Rubin et al. |
| 7,008,399 B2 | 3/2006 | Larsen et al. |
| 7,011,649 B2 | 3/2006 | De La Serna et al. |
| 7,041,085 B2 | 5/2006 | Perez et al. |
| 7,066,909 B1 | 6/2006 | Peter et al. |
| 7,094,230 B2 | 8/2006 | Flaherty et al. |
| 7,104,400 B2 | 9/2006 | Kiehne |
| 7,118,553 B2 | 10/2006 | Scherer |
| 7,226,450 B2 | 6/2007 | Athanasiou et al. |
| 7,255,684 B2 | 8/2007 | Zubry |
| 7,273,469 B1 | 9/2007 | Chan et al. |
| 7,290,573 B2 | 11/2007 | Py et al. |
| 7,297,135 B2 | 11/2007 | Jeffrey |
| 7,297,136 B2 | 11/2007 | Wyrick |
| 7,357,790 B2 | 4/2008 | Hommann et al. |
| 7,361,160 B2 | 4/2008 | Hommann et al. |
| 7,370,759 B2 | 5/2008 | Hommann |
| 7,381,201 B2 | 6/2008 | Gilbert et al. |
| 7,500,963 B2 | 3/2009 | Westbye et al. |
| 7,635,348 B2 | 12/2009 | Raven et al. |
| 7,648,483 B2 | 1/2010 | Edwards et al. |
| 7,654,987 B2 | 2/2010 | Hommann et al. |
| 7,731,686 B2 | 6/2010 | Edwards et al. |
| 7,922,695 B2 | 4/2011 | Wiegel et al. |
| 8,012,125 B1 | 9/2011 | Fago et al. |
| 8,052,645 B2 | 11/2011 | Slate et al. |
| 2001/0005781 A1 * | 6/2001 | Bergens et al. ............... 604/208 |
| 2003/0036725 A1 | 2/2003 | Lavi et al. |
| 2003/0050592 A1 | 3/2003 | Slate et al. |
| 2003/0105430 A1 | 6/2003 | Lavi et al. |
| 2003/0236502 A1 | 12/2003 | De La Serna et al. |
| 2004/0039336 A1 | 2/2004 | Amark et al. |
| 2004/0054327 A1 | 3/2004 | Gillespie |
| 2004/0068266 A1 * | 4/2004 | Delmotte ....................... 606/92 |
| 2004/0116861 A1 | 6/2004 | Trocki et al. |
| 2004/0133154 A1 | 7/2004 | Flaherty et al. |
| 2004/0133162 A1 | 7/2004 | Trocki et al. |
| 2004/0153008 A1 | 8/2004 | Sharf et al. |
| 2004/0225262 A1 | 11/2004 | Fathallah et al. |
| 2005/0027255 A1 | 2/2005 | Lavi et al. |
| 2005/0033242 A1 | 2/2005 | Perez et al. |
| 2005/0049561 A1 | 3/2005 | Hommann et al. |
| 2005/0054987 A1 | 3/2005 | Perez et al. |
| 2005/0080377 A1 | 4/2005 | Sadowski et al. |
| 2005/0165404 A1 | 7/2005 | Miller |
| 2005/0171476 A1 | 8/2005 | Judson et al. |
| 2005/0171477 A1 | 8/2005 | Rubin et al. |
| 2005/0203466 A1 | 9/2005 | Hommann et al. |
| 2005/0209569 A1 | 9/2005 | Ishikawa et al. |
| 2005/0277885 A1 | 12/2005 | Scherer |
| 2006/0030819 A1 | 2/2006 | Young et al. |
| 2006/0270985 A1 | 11/2006 | Hommann et al. |
| 2007/0021720 A1 | 1/2007 | Guillermo |
| 2007/0066938 A1 | 3/2007 | Iio et al. |
| 2007/0100281 A1 | 5/2007 | Morris et al. |
| 2007/0112301 A1 | 5/2007 | Preuthun et al. |
| 2007/0112310 A1 | 5/2007 | Lavi et al. |
| 2007/0118081 A1 | 5/2007 | Daily et al. |
| 2007/0135767 A1 | 6/2007 | Gillespie et al. |
| 2007/0142787 A1 | 6/2007 | Scherer |
| 2007/0149925 A1 | 6/2007 | Edwards et al. |
| 2007/0173770 A1 | 7/2007 | Stamp |
| 2007/0197968 A1 | 8/2007 | Pongpairochana et al. |
| 2007/0219498 A1 | 9/2007 | Malone et al. |
| 2007/0233001 A1 | 10/2007 | Burroughs et al. |
| 2007/0239114 A1 | 10/2007 | Edwards et al. |
| 2007/0265568 A1 | 11/2007 | Tsals et al. |
| 2008/0039795 A1 | 2/2008 | Slate et al. |
| 2008/0051711 A1 | 2/2008 | Mounce et al. |
| 2008/0051714 A1 | 2/2008 | Moberg et al. |
| 2008/0051715 A1 | 2/2008 | Young et al. |
| 2008/0132841 A1 | 6/2008 | Chiwanga et al. |
| 2008/0140007 A1 | 6/2008 | Glynn |
| 2008/0262434 A1 | 10/2008 | Vaillancourt |
| 2008/0312602 A1 | 12/2008 | Barrow-Williams et al. |
| 2009/0018494 A1 | 1/2009 | Nemoto et al. |
| 2009/0018505 A1 | 1/2009 | Arguedas et al. |
| 2009/0024112 A1 | 1/2009 | Edwards et al. |
| 2009/0043253 A1 | 2/2009 | Podima et al. |
| 2009/0149744 A1 | 6/2009 | Nemoto et al. |
| 2009/0312705 A1 | 12/2009 | Grunhut et al. |
| 2009/0322545 A1 | 12/2009 | Gibson |
| 2010/0016795 A1 | 1/2010 | Mcloughlin |
| 2010/0036318 A1 | 2/2010 | Raday et al. |
| 2010/0152655 A1 | 6/2010 | Stamp |
| 2010/0160894 A1 | 6/2010 | Julian et al. |

| | | | |
|---|---|---|---|
| 2010/0198060 A1 | 8/2010 | Fago et al. | |
| 2010/0312195 A1 | 12/2010 | Johansen et al. | |
| 2011/0004165 A1 | 1/2011 | Iio et al. | |
| 2011/0097229 A1 | 4/2011 | Cauley Iii et al. | |
| 2011/0137286 A1 | 6/2011 | Mudd et al. | |
| 2011/0152781 A1 | 6/2011 | Brunnberg et al. | |
| 2011/0160580 A1 | 6/2011 | Perkins et al. | |
| 2011/0166512 A1 | 7/2011 | Both et al. | |
| 2011/0184383 A1 | 7/2011 | Hasegawa | |
| 2011/0190693 A1 | 8/2011 | Takatsuka et al. | |
| 2011/0190702 A1 | 8/2011 | Stumber | |
| 2011/0202011 A1 | 8/2011 | Wozencroft | |
| 2011/0224616 A1 | 9/2011 | Slate et al. | |
| 2011/0224620 A1 | 9/2011 | Johansen et al. | |
| 2011/0224621 A1 | 9/2011 | Johansen et al. | |
| 2011/0230833 A1 | 9/2011 | Landman et al. | |
| 2011/0257596 A1 | 10/2011 | Gaudet | |
| 2011/0264046 A1 | 10/2011 | Nyholm et al. | |

FOREIGN PATENT DOCUMENTS

| | | |
|---|---|---|
| WO | 8703494 A1 | 6/1987 |
| WO | 8707160 A1 | 12/1987 |
| WO | 9118634 A1 | 12/1991 |
| WO | 9206725 | 4/1992 |
| WO | 9208506 A1 | 5/1992 |
| WO | 9221392 A1 | 12/1992 |
| WO | 9302728 A1 | 2/1993 |
| WO | 9313817 A1 | 7/1993 |
| WO | 9324160 A1 | 12/1993 |
| WO | 9325256 A1 | 12/1993 |
| WO | 9406494 A1 | 3/1994 |
| WO | 9521645 A1 | 8/1995 |
| WO | 9525555 A1 | 9/1995 |
| WO | 9531235 A1 | 11/1995 |
| WO | 9534333 A2 | 12/1995 |
| WO | 9600594 A1 | 1/1996 |
| WO | 9621482 A2 | 7/1996 |
| WO | 9626754 A2 | 9/1996 |
| WO | 9638190 A1 | 12/1996 |
| WO | 9707839 A1 | 3/1997 |
| WO | 9731665 A1 | 9/1997 |
| WO | 9813077 A2 | 4/1998 |
| WO | 9817332 A2 | 4/1998 |
| WO | 9821408 A1 | 5/1998 |
| WO | 9917823 A1 | 4/1999 |
| WO | 9920327 A1 | 4/1999 |
| WO | 9921600 A2 | 5/1999 |
| WO | 0002605 A1 | 1/2000 |
| WO | 0009186 A2 | 2/2000 |
| WO | 0024441 A1 | 5/2000 |
| WO | 0025846 A2 | 5/2000 |
| WO | 0100261 A1 | 1/2001 |
| WO | 0137903 A2 | 5/2001 |
| WO | 0141835 A2 | 6/2001 |
| WO | 0189634 A2 | 11/2001 |
| WO | 0207812 A2 | 1/2002 |
| WO | 0249691 A2 | 6/2002 |
| WO | 02092153 A2 | 11/2002 |
| WO | 03006099 A1 | 1/2003 |
| WO | 03008023 A1 | 1/2003 |
| WO | 03047663 A2 | 6/2003 |
| WO | 03090509 A2 | 11/2003 |
| WO | 03103749 A2 | 12/2003 |
| WO | 2004069303 A2 | 8/2004 |
| WO | 2004108193 A1 | 12/2004 |
| WO | 2005053771 A2 | 6/2005 |
| WO | 2005070481 A1 | 8/2005 |
| WO | 2005079440 A2 | 9/2005 |
| WO | 2005094923 A1 | 10/2005 |
| WO | 2006015501 A1 | 2/2006 |
| WO | 2006017732 A2 | 2/2006 |
| WO | 2006020609 A1 | 2/2006 |
| WO | 2006062788 A2 | 6/2006 |
| WO | 2006063015 A2 | 6/2006 |
| WO | 2006086774 A2 | 8/2006 |
| WO | 2007002053 A2 | 1/2007 |
| WO | 2007044980 A2 | 4/2007 |
| WO | 2007047200 A1 | 4/2007 |
| WO | 2007053779 A2 | 5/2007 |
| WO | 2007075677 A2 | 7/2007 |
| WO | 2007099044 A1 | 9/2007 |
| WO | 2007126851 A2 | 11/2007 |
| WO | 2007138299 A1 | 12/2007 |
| WO | 2007140610 A1 | 12/2007 |
| WO | 2008021776 A2 | 2/2008 |
| WO | 2008024810 A2 | 2/2008 |
| WO | 2008048750 A2 | 4/2008 |
| WO | 2008064092 A2 | 5/2008 |
| WO | 2008075033 A1 | 6/2008 |
| WO | 2008083313 A2 | 7/2008 |
| WO | 2008093063 A2 | 8/2008 |
| WO | 2008094984 A2 | 8/2008 |
| WO | 2008095124 A1 | 8/2008 |
| WO | 2008107670 A2 | 9/2008 |
| WO | 2008139458 A2 | 11/2008 |
| WO | 2008139460 A2 | 11/2008 |
| WO | 2008146021 A1 | 12/2008 |
| WO | 2009006725 A1 | 1/2009 |
| WO | 2009019437 A1 | 2/2009 |
| WO | 2009143255 A1 | 11/2009 |
| WO | 2010076275 A1 | 7/2010 |
| WO | 2010091133 A2 | 8/2010 |
| WO | 2010100213 A1 | 9/2010 |
| WO | 2010127449 A1 | 11/2010 |
| WO | 2011057065 A1 | 5/2011 |

OTHER PUBLICATIONS

International Application No. PCT/US09/44693, filed May 20, 2009, entitled, "Autoinjector System", Slate, et al.

International Search Report issued for International Application No. PCT/US09/44693 filed May 20, 2009.

Written Opinion of the International Searching Authority issued for International Application No. PCT/US09/44693 filed May 20, 2009.

Office Action dated Dec. 22, 2010 issued in co-pending U.S. Appl. No. 12/178,447, filed Jul. 23, 2008.

Office Action dated Mar. 30, 2010 issued in co-pending U.S. Appl. No. 12/178,447, filed Jul. 23, 2008.

Office Action dated Oct. 15, 2009 issued in co-pending U.S. Appl. No. 12/178,447, filed Jul. 23, 2008.

Notice of Allowance dated Apr. 6, 2011 issued in co-pending U.S. Appl. No. 12/178,447, filed Jul. 23, 2008.

Notice of Allowance dated Jun. 24, 2011 issued in co-pending U.S. Appl. No. 12/178,447, filed Jul. 23, 2008.

Notice of Allowance dated Jun. 24, 2011, issued in co-pending U.S. Appl. No. 12/178,447 filed Jul. 23, 2008 of John B. Slate.

* cited by examiner

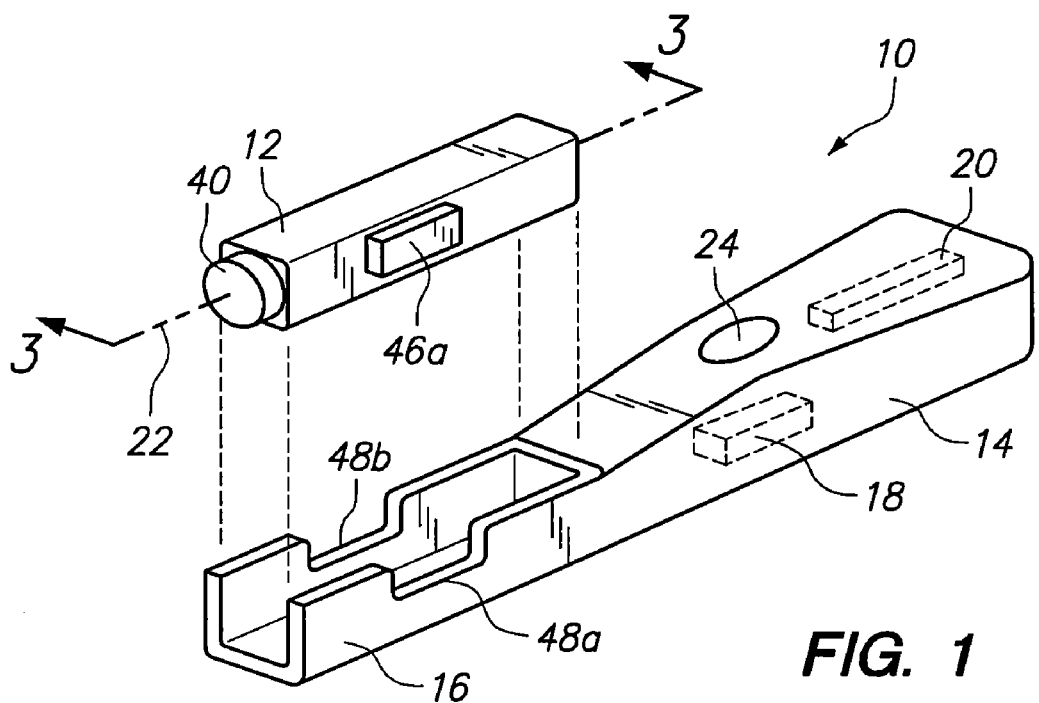
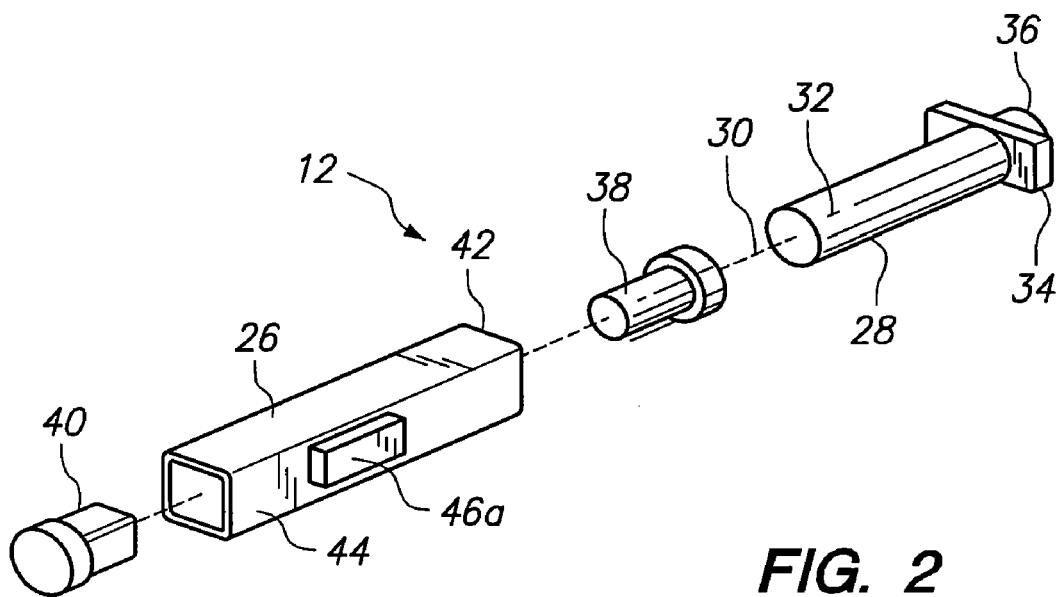

CASSETTE FOR A HIDDEN INJECTION NEEDLE

FIELD OF THE INVENTION

The present invention pertains generally to systems for injecting fluid medicaments into a patient from a pre-filled hypodermic syringe. More particularly, the present invention pertains to systems wherein the needle of the hypodermic syringe remains concealed and hidden during an injection procedure. The present invention is particularly, but not exclusively, useful as a system wherein a hypodermic syringe is concealed in a cassette; wherein the cassette is engageable with a drive mechanism; and wherein the drive mechanism uses one motor to present the syringe needle for an injection, and uses another motor to expel fluid medicament through the syringe needle.

BACKGROUND OF THE INVENTION

Pre-filled hypodermic syringes provide several advantages for the home-use market. These advantages include the fact that pre-filled syringes can be prepared for each fluid medicament with the exactly required dosage. Further, they are easily operated, by merely advancing the stopper of the syringe. Aside from the costs of the particular medication that is being used, pre-filled syringes are also economically manufactured. A consequence of all this is that pre-filled syringes have commercial appeal. Nevertheless, pre-filled syringes also have a significant drawback in the marketplace. Specifically, many users are either frightened by an exposed needle or feel they are inherently incapable of performing an injection.

Because of aversions to exposed needles, as well as the many health and safety issues that may be involved, various needleless injectors and other devices have been developed for the specific purpose of concealing needles from the user. Typically, for devices where hidden or protected needles are employed, the devices are spring-operated and tend toward the use of cartridges, rather than the use of pre-filled hypodermic syringes. For example, U.S. Pub. No. 2007/0021720A1 which was filed for an invention entitled "Injector", discloses such a device employing a variety of spring activated mechanisms. When springs are employed, however, the forces cannot be varied from application to application. This can be particularly problematic in situations where it may be desirable to use a same device, at different times, to inject different medications, with different fluid viscosities. Indeed, it may not be possible to use a same spring-loaded injector for different medications. The situation can become further complicated when consideration is given to the fact that, in a single injection procedure, the optimal force for inserting a syringe needle into a patient may be quite different from the force required to subsequently expel fluid medicament from the syringe. Furthermore, the starting force of a spring will differ from the ending force. And, this can be problematic for assuring a complete drug delivery.

In light of the above, it is an object of the present invention to provide a system using disposable cassettes that are pre-loaded with pre-filled syringes to hide the syringe needle during its use. Another object of the present invention is to provide a system for injecting fluid medicaments into a patient that uses different motors to accommodate different force requirements during an injection procedure. Still another object of the present invention is to provide a system for injecting a fluid medicament to a patient that is easy to assemble, is simple to use, and is comparatively cost effective.

SUMMARY OF THE INVENTION

In accordance with the present invention, a system for injecting fluid medicaments into a patient from a pre-filled hypodermic syringe, employs a cassette that is pre-loaded with the pre-filled syringe. For this combination, the hypodermic syringe can be loaded into the cassette during manufacture, or be subsequently loaded by a contract service provider. In either case, the syringe needle is concealed inside the cassette and hidden from the view of the end-user. Importantly, the only preparation required by the end-user (e.g. the patient that is to self-administer the fluid medicament) is to mount the cassette onto a drive mechanism.

Structurally, the system of the present invention envisions a pre-filled syringe that will have a needle, and it will have a stopper for expelling the fluid medicament from the syringe through the needle. Further, the pre-filled syringe will be firmly held on the cassette in a position where the syringe needle is concealed and hidden from view. As envisioned for the present invention, the pre-filled hypodermic syringe can be firmly held in the concealed position, in any of several different ways. These include, the use of a latching mechanism, an adhesive, or a flexible abutment.

Once the cassette has been loaded with the pre-filled hypodermic syringe, the cassette can be engaged with a drive mechanism. In detail, the drive mechanism includes two separate motors that perform two different functions. A first motor is provided for engaging the syringe in its concealed position where its needle is hidden. With this engagement, the first motor then moves the syringe and its needle from the concealed position and into an exposed position where the needle is extended for insertion into the patient. While the needle is inserted into the patient, a second motor is provided for pushing the stopper on the syringe to expel fluid medicament from the syringe. After the injection has been completed, the first motor then withdraws the syringe and its needle back into the concealed position. Importantly, after it has been withdrawn the syringe is again firmly held in the concealed position, inside the cassette. Thus, the needle remains hidden from view at all times during an injection procedure. Further, as noted above, the syringe is firmly held inside the cassette to insure the syringe needle does not inadvertently extend from the cassette.

In operation, an end-user mounts a pre-loaded cassette on the drive mechanism. The end-user then removes a protective cover from the syringe needle and positions the system at a site where an injection is to be made. A button on the system is then pushed to activate the drive mechanism for an injector procedure. After the injection has been completed, the cassette, with its now empty syringe, can be removed from the drive mechanism and discarded.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 1 is a perspective view of a cassette and associated drive mechanism for a system of the present invention;

FIG. 2 is an exploded perspective view of the cassette with a pre-loaded, pre-filled hypodermic syringe;

DESCRIPTION OF THE PREFERRED EMBODIMENTS

Figure 3A:
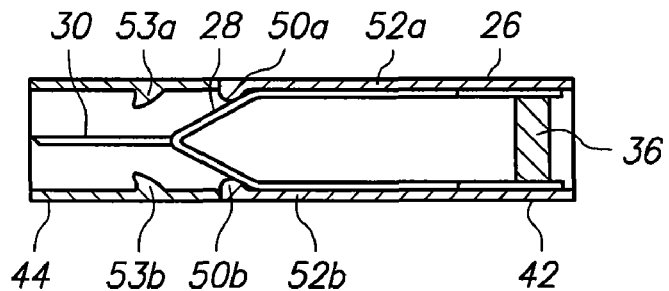
FIG. 3A is a cross-sectional view of a pre-loaded cassette, as seen along the line 3-3 in FIG. 1, with a pre-filled hypodermic syringe in a withdrawn (proximal) position.

Referring initially to FIG. 1, a system for injecting a fluid medicament into a patient is shown and is generally designated 10. In detail, FIG. 1 shows the system 10 includes a cassette 12 and a drive mechanism 14. Further, the drive mechanism 14 is formed with a cradle 16 that is dimensioned to receive and hold the cassette 12 on the drive mechanism 14. It is also indicated in FIG. 1 that the drive mechanism 14 includes a first motor 18 (shown in phantom) and a second motor 20 (also shown in phantom). For purposes of the present invention, the motors 18 and 20 can be of any standard type well known in the art (e.g. a lead screw). More specifically, the motors 18 and 20 must be capable of individually exerting axially directed forces on contents of the cassette 12. These forces will need to be directed substantially along the axis 22. Activation of the motors 18 and 20 for the generation of these forces is accomplished by manipulation of the button 24.

Structurally, the cassette 12 and its interaction with associated contents are shown in FIG. 2. There it will be seen that the cassette 12 is essentially a housing 26 having hollow, tubular shaped structure. Importantly, the housing 26 is provided to hold a hypodermic syringe 28 having a needle 30 that is affixed to the distal end of its fluid chamber 32. A standard grip 34 is provided at the proximal end of the fluid chamber 32. Also, a stopper 36 is provided to expel fluid medicament from the fluid chamber 32 through the needle 30. A protective cover 38 can be provided to cover the needle 30 when system 10 is not in operational use, and a cap 40 is employed to grip the protective cover 38.

Prior to an operation of the system 10, the cassette 12 is pre-loaded. And, furthermore, the syringe 28 is pre-filled with an appropriate dose of the desired fluid medicament. Before pre-loading the cassette 12, the protective cover 38 is positioned over the needle 30 on syringe 28. The pre-filled syringe 28 is then inserted into the housing 26 through its proximal end 42. The cap 40 can then be inserted through the distal end 44 of the housing 26 to engage the cap 40 with the protective cover 38. The cassette 12 is thus pre-loaded, and it will appear substantially as shown in FIG. 1. Once it has been pre-loaded, the cassette 12 can be mounted on the drive mechanism 14 is indicated in FIG. 1. This is done by merely inserting the cassette 12 into cradle 16. During this insertion the protrusions 46a and 46b (protrusion 46b is not shown) engage with respective recesses 48a and 48b to stabilize the cassette 12 on drive mechanism 14.

Figure 3B:
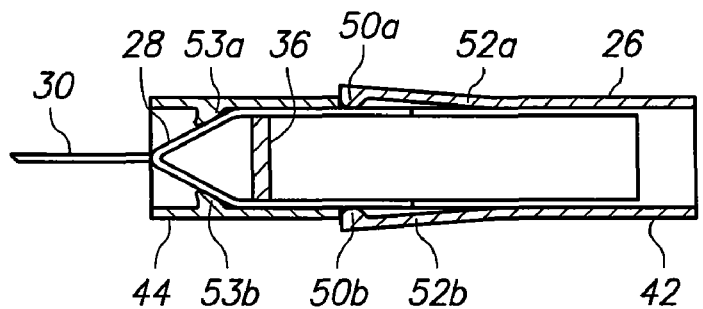
FIG. 3B is a view of the cassette shown in FIG. 3A with the syringe in an extended (distal) position after drug delivery.

An important structural aspect of the present invention is that when the pre-filled syringe 28 has been pre-loaded into the cassette 12, it will thereafter be firmly held inside the cassette 12. Specifically, it will be held in a position where the needle 30 is concealed inside the cassette 12 and thereby hidden from view. For example, FIG. 3A shows a syringe 28 being held in the housing 26 of a cassette 12 by opposed bumps 50a and 50b that are formed onto respective resilient arms 52a and 52b. While syringe 28 is in the position shown in FIG. 3A (sometimes referred to hereinafter as the concealed position or proximal position), the syringe needle 30 is hidden inside the housing 26. Also, until, the bumps 50a and 50b have been overcome by an axial force exerted by the syringe 28 and supplied by the first motor 18, the syringe 28 will be firmly held in its concealed position. FIG. 3B then shows that when a sufficient force has been applied by the first motor 18, the syringe 28 will move from its concealed (proximal) position, and into an extended (distal) position. In this distal position, the syringe 28 is retained in the cassette 12 by stops 53a and 53b while the needle 30 extends from the housing 26 for insertion into a patient. Importantly, the first motor 18 is attached to the syringe 28 in a manner that allows the first motor 18 to retract the syringe 28 from the extended (distal) position, and thereby return the needle 30 to its concealed (proximal) position. Again, the syringe 28 will be firmly held on the housing 26 by the bumps 50a and 50b.

Although the disclosure for the present invention is directed primarily toward a dual motor system (i.e. first motor 18 and second motor 20), two motors may not be necessary. Indeed, it will be readily appreciated by a person skilled in the art that a single motor may suffice for purposes of the present invention. In such a case, however, an appropriate transmission will be required for alternating between creating forces directly on the syringe 28 or on the stopper 36. In any event, the importance of using motors for system 10, vis-à-vis springs, is to generate controllable and reliable forces for movements of the syringe 28, or for expelling fluid medicament therefrom.

Figure 4:
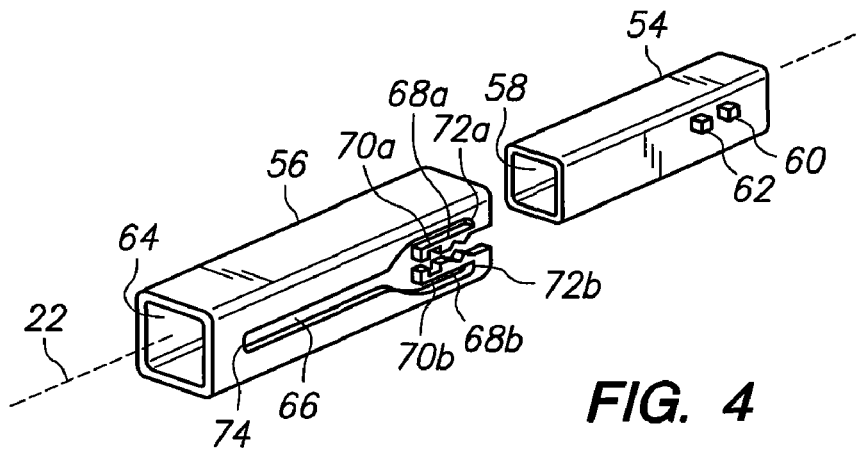
FIG. 4 is an exploded perspective view of another embodiment of a cassette for use with the present invention.

An alternate construction for the cassette 12 is shown in FIG. 4. There an embodiment for the cassette 12 is seen that includes an inner sleeve 54 and an outer sleeve 56. More specifically, the inner sleeve 54 is a hollow, substantially tube-shaped structure that is formed with a lumen 58. Formed onto the outside of the inner sleeve 54 are a proximal projection 60 and a distal projection 62 that are axially aligned with each other. FIG. 4 also shows that the outer sleeve 56, like inner sleeve 54, is hollow and substantially tube-shaped. Further, the outer sleeve 56 is formed with a lumen 64 and an axially aligned slot 66. Resilient arms 68a and 68b are formed on the outer sleeve 56 and are positioned to extend in the slot 66, substantially as shown. Additionally, the resilient arms 68a and 68b are respectively formed with detents 70a and 70b and ramps 72a and 72b.

In order to load a cassette 12 having the embodiment shown in FIG. 4, the inner sleeve 54 is inserted into the lumen 64 of the outer sleeve 56. Importantly, with this insertion the proximal projection 60 on inner sleeve 54 is positioned and held in the detents 70a and 70b of the arms 68a and 68b. The hypodermic syringe 28 can then be inserted into the lumen 58 of the inner sleeve 54. This places the syringe 28 in its concealed (proximal) position on the cassette 12. Subsequently, movement of the syringe 28 from its concealed (proximal) position to its extended (distal) position is accomplished by the first motor 18. More specifically, a bar (not shown) which is operated by the first motor 18, is used to urge against the ramps 72a and 72b on arms 68a and 68b. This causes the arms 68a and 68b to spread and thereby release the proximal projection 60 from their grasp. The inner sleeve 54, with syringe 28 firmly held thereon, can then be moved in a distal direction through the lumen 64 of the outer sleeve 56. This distal movement continues until the distal projection 62 contacts the end abutment 74 of the slot 66. The syringe 28 is now in its extended (distal) position. Subsequently, the first motor 18 can withdraw the inner sleeve 54 in a proximal direction through the lumen 64 of the outer sleeve 56. This proximal movement continues until the proximal projection 60 on inner sleeve 54 again engages with the detents 70*a* and 70*b*. Thus, the syringe 28 is returned to its concealed (proximal) position inside the cassette 12.

Figure 5:
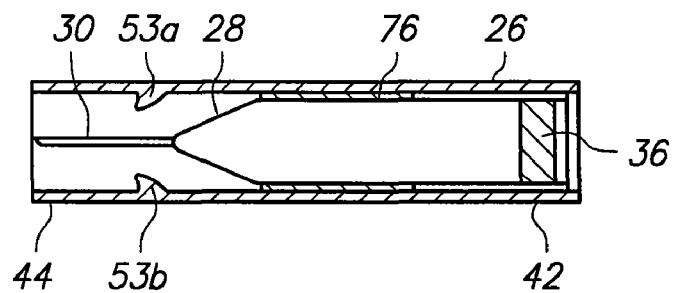
FIG. 5 is a cross-sectional view of an alternate embodiment of a pre-loaded cassette, as seen along the line 3-3 in FIG. 1.

FIG. 5 shows yet another embodiment for the cassette 12 of the present invention wherein an adhesive 76 is positioned on the cassette 12 to firmly hold the syringe 28 in its concealed (proximal) position. The adhesive 76, or a similar type of restraining element, can be used either directly between the syringe 28 and cassette 12 as shown in FIG. 5, or in some arrangement between the inner sleeve 54 and outer sleeve 56 when an embodiment as shown in FIG. 4 is employed. Alternatively, an arrangement such as disclosed in FIGS. 3A and 3B can also be used for an embodiment as shown in FIG. 4. The import here is that for an embodiment for the cassette 12 having an inner sleeve 54 and an outer sleeve 56, a structure other than the arms 68*a* and 68*b* can be used. In particular, an adhesive 76 or bumps 50*a,b* can be used in lieu of the arms 68*a* and 68*b* to hold the syringe 28 in its concealed (proximal) position.

In the operation of the system 10 of the present invention, a pre-loaded cassette 12 is positioned in the cradle 16 on the drive mechanism 14. This engages the syringe 28 with the drive mechanism 14. Prior to an injection, the cap 40 is removed from the system 10. More specifically, because the cap 40 is attached to the protective cover 38 over needle 30 of the syringe 28, the protective cover 38 is also removed. The system 10 is now ready for an injection.

With the system 10 positioned at an injection site (not shown), the button 24 on drive mechanism 14 is depressed. Depression of the button 24 causes the first motor 18 to engage with the syringe 28 and to move the syringe 28 from its concealed (proximal) position to its extended (distal) position. This causes the needle 30 of syringe 28 to penetrate into tissue of the patient for an injection. At this point, the second motor 20 pushes on stopper 36 to expel fluid medicament from the fluid chamber 32 of the syringe 28. After an injection has been completed, the first motor 18 is again activated. This time, however, instead of advancing the syringe 28, it withdraws the syringe 28 from the extended (distal) position to the concealed (proximal) position. The cassette 12, along with the expended syringe 28, can then be removed from the drive mechanism 14 and discarded.

While the particular Cassette for a Hidden Injection Needle as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A system for injecting a fluid medicament into a patient, the system comprising:
    a drive mechanism;
    a hypodermic syringe pre-filled with the fluid medicament; and
    a cassette for receiving and holding the hypodermic syringe;
    wherein the drive mechanism comprises a cradle, a first motor, and a second motor;
    wherein the syringe comprises a needle, and a stopper for expelling the medicament from the syringe through the needle;
    wherein the first motor of the drive mechanism is for moving the syringe in the cassette between a first position and a second position when the cassette is mounted in the cradle of the drive mechanism, the first position being a proximal position for hiding the syringe needle inside the cassette, and the second position being a distal position where the needle extends from the cassette for injection of the medicament;
    wherein the second motor is for pushing the stopper to expel the medicament from the syringe while the syringe is in the distal position; and
    wherein the cassette comprises:
        an inner sleeve for holding the syringe
        an outer sleeve comprising a hollow tube having a wall defining an axis, and having a first end and a second end, with the wall of the tube having a longitudinal slot extending between the first and second ends of the tube, the outer sleeve for supporting the inner sleeve during movement of the inner sleeve thereon between the proximal position and the distal position, with the inner sleeve being selectively engaged with the outer sleeve to firmly hold the inner sleeve in the proximal position, and engageable with the first motor of the drive mechanism for release of the inner sleeve from the outer sleeve and subsequent movement of the syringe with the inner sleeve between the proximal position and the distal position;
        a resilient arm formed on the wall of the outer sleeve with a detent formed on the arm, the arm being biased to extend the detent into the slot of the outer sleeve; and
        a projection extending radially outward from the inner sleeve and into the slot of the outer sleeve for selective engagement with the detent of the outer sleeve.

2. A system as recited in claim 1 further comprising a pair of resilient arms, wherein the arms are opposite each other across the slot for concerted engagement with the projection on the inner sleeve.

3. A system as recited in claim 1 further comprising:
    a protective cover positioned over the needle of the syringe; and
    a cap engageable with the protective cover for subsequent removal of the protective cover with the cap when the cap is removed from the outer sleeve.

4. A system as recited in claim 1 further comprising an adhesive on the cassette to hold the hypodermic syringe in the proximal position for selective release therefrom, and re-engagement therewith, in response to action of the drive mechanism.

5. A system as recited in claim 1 further comprising a resilient bump formed on the cassette to hold the syringe in the proximal position, and to release the syringe therefrom in response to action of the drive mechanism.

6. A system for expelling a fluid medicament from a pre-filled hypodermic syringe, wherein the syringe has a needle and a stopper for expelling the medicament from the syringe through the needle, the system comprising:
    a cassette for holding the syringe in a first position to hide the needle,
    a cradle for receiving the cassette;
    a first motor for moving the syringe from the first position to a second position wherein the needle extends from the cassette for injection of the medicament; and
    a second motor for pushing the stopper to expel the medicament from the syringe while the syringe is in the second position;
    wherein the cassette comprises:
        an inner sleeve for holding the syringe;
        an outer sleeve for supporting the inner sleeve during movement of the inner sleeve thereon between the first position and the second position, the outer sleeve comprising a hollow tube having a wall defining an axis, and having a first end and a second end, with the wall of the tube having a longitudinal slot extending between the first and second ends of the tube; and a resilient arm formed on the wall of the outer sleeve with a detent formed on the arm, the arm being biased to extend the detent into the slot of the outer sleeve; and a projection extending radially outward from the inner sleeve and into the slot of the outer sleeve for selective engagement with the detent of the outer sleeve; and wherein the first and second motors form a drive mechanism, the inner sleeve being selectively engaged with the outer sleeve to firmly hold the inner sleeve in the first position, and engageable with the drive mechanism for release of the inner sleeve from the outer sleeve and subsequent movement of the syringe with the inner sleeve between the first position and the second position.

* * * * *